US008076060B2

(12) United States Patent (10) Patent No.: US 8,076,060 B2
Chynn (45) Date of Patent: Dec. 13, 2011

(54) VACCINATION AND IMMUNOTHERAPY AS NEW THERAPEUTIC MODALITIES IN THE TREATMENT OF GLAUCOMA

(76) Inventor: Emil William Chynn, New York, NY (US)

(*) Notice: Subject to any disclaimer, the term of this patent is extended or adjusted under 35 U.S.C. 154(b) by 1635 days.

(21) Appl. No.: 10/910,596

(22) Filed: Aug. 3, 2004

(65) Prior Publication Data

US 2005/0031640 A1 Feb. 10, 2005

Related U.S. Application Data

(60) Provisional application No. 60/492,151, filed on Aug. 4, 2003.

(51) Int. Cl.
*C07Q 1/70* (2006.01)
*C12Q 1/00* (2006.01)
*A61K 39/00* (2006.01)
*A61K 39/21* (2006.01)

(52) U.S. Cl. .............. 435/4; 435/5; 424/184; 424/188.1

(58) Field of Classification Search .................. None
See application file for complete search history.

(56) References Cited

U.S. PATENT DOCUMENTS

| | | | |
|---|---|---|---|
| 4,952,581 | A | 8/1990 | Bito et al. |
| 5,334,394 | A | 8/1994 | Kossovsky et al. |
| 5,516,796 | A | 5/1996 | Stjernschantz et al. |
| 5,658,569 | A | 8/1997 | Osther et al. |
| 5,741,492 | A | 4/1998 | Hurwitz et al. |
| 5,741,810 | A | 4/1998 | Burk |
| 5,763,160 | A | 6/1998 | Wang |
| 5,846,546 | A | 12/1998 | Hurwitz et al. |
| 5,861,243 | A | 1/1999 | Dietrich et al. |
| 5,928,930 | A | 7/1999 | Salk et al. |
| 5,981,276 | A | 11/1999 | Sodroski et al. |
| 6,017,543 | A | 1/2000 | Salk et al. |
| 6,090,392 | A | 7/2000 | Berman |
| 6,096,902 | A | 8/2000 | Burk |
| 6,218,428 | B1 | 4/2001 | Chynn |
| 6,331,404 | B1 | 12/2001 | Berman et al. |
| 6,350,467 | B1 | 2/2002 | Demopoulos et al. |

OTHER PUBLICATIONS

Russell ND et al. "Phase 2 study of an HIV-1 canarypox vaccine (vCP1452) alone and in combination with rgp120: negative results fail to trigger a phase 3 correlates trial." J Acquir Immune Defic Syndr. Feb. 1, 2007;44(2):203-12.*
Jones NG, et al. "AIDSVAX immunization induces HIV-specific CD8+ T-cell responses in high-risk, HIV-negative volunteers who subsequently acquire HIV infection." Vaccine. Dec. 9, 2008[Epub ahead of print] pp. 1-5.*
Tezel G, Wax MB. "Glaucoma" Chem Immunol Allergy. 2007;92:221-7. Review.*
Wax MB."Is there a role for the immune system in glaucomatous optic neuropathy?" Curr Opin Ophthalmol. Apr. 2000;11(2):145-50. Review.*

Vecino E "Animal models in the study of glaucoma: past, present and future" ARCH SOC ESP OFTALMOL 2008; 83: 517-520.*
Galatt, Kirk "Animal models for glaucoma" Invest. Ophthalmol. Visual Sci. 16(7):592-596; 1977.*
Mermoud A. et al. "Animal model for uveitic glaucoma" Grafe's Arch Clin Exp Ophthalmol. 232:553-560; 1994.*
Letvin N. et al. "Potent, protective anti-HIV immune responses generated by bimodal HIV envelope DNA plus protein vaccination" Proc. Natl. Acad. Sci. USA vol. 94, pp. 9378-9383, Aug. 1997.*
Arevalo JF, et al, "Correlation between intraocular pressure and CD4+ T-lymphocyte counts in patients with human immunodeficiency virus with and without cytomegalovirus retinitis", Am J Ophthalmol, 122(1): 91-6 (1996).
Cartwright et al., "Immune-related disease and normal-tension glaucoma: a case-control study", Arch Ophthalmol, 110(4): 500-2 (1992).
Fineman et al., "Bilateral choroidal effusions and angle-closure glaucoma associated with human immunodeficiency virus infection", Retina, 17(5): 455-7 (1997).
Haynes et al., "The Current Status of HIV-1 Vaccine Development 2004", Resources section of the National Institute of Allergy and Infectious Disease (NIAID) website www.niaid.nih.gov, pp. 1-32 (2004).
Johnston et al., "Progress in HIV vaccine development", Current Opinion in Pharmacol, 1:504-510 (2001).
Kipnis et al., "T cell immunity to copolymer 1 confers neuroprotection on the damaged optic nerve: possible therapy for optic neuropathies", Proc Natl Acad Sci USA, Jun 20: 97(13): 7446-51 (2000).
Loewen et al., "Genetic modification of human trabecular meshwork with lentiviral vectors", Hum Gene Ther, 12(17): 2109-19 (2001).
Nagasubramanian et al., "Immunological investigations in chronic simple glaucoma", Trans Ophthalmol Soc UK, 98(1): 22-7 (1978).
Nash et al., "Bilateral angle-closure glaucoma associated with uveal effusion: presenting sign of HIV infection", Surv Ophthalmol, 36(4): 255-8 (1992).
Polansky et al., "Cellular Mechanisms Influencing the Aqueous Outflow Pathway", Principles and Practice of Ophthalmology, Albert et al. Eds., pp. 226-251 (1994).
Schori et al., "Vaccination for protection of retinal ganglion cells against death from glutamate cytotoxicity and ocular hypertension: implications for glaucoma", Proc Natl Acad Sci USA, 98(6): 3398-403 (2001).
Schwartz et al., "Potential treatment modalities for glaucomatous neuropathy: neuroprotection and neuroregeneration", J Glaucoma (Dec; 5(6): 427-32 (1996).
The Jordan Report 20th Anniversary Accelerated Development of Vaccines 2002: Division of Microbiology and Infectious Diseases, National Institute of Allergy and Infectious Disease, National Institutes of Health (2002).

(Continued)

*Primary Examiner* — Bo Peng
(74) *Attorney, Agent, or Firm* — James S. McDonald

(57) ABSTRACT

This invention provides a method whereby a vaccine, particularly a vaccine based on a prophylactic or therapeutic AIDS/HIV vaccine, or other immune-reactive substance is administered to produce an immunologic response that decreases intraocular pressure or has a neuro-protective effect beneficial in the treatment of glaucoma patients. The invention may also be used as a provocative test to diagnose glaucoma as well as identify those patients at risk for developing glaucoma. The invention may also be used to prevent the development of glaucoma in patients deemed to be at high risk of developing glaucoma, such as glaucoma suspects or ocular hypertensive patients.

11 Claims, No Drawings

OTHER PUBLICATIONS

Ullman et al., "Bilateral angle-closure glaucoma in association with the acquired immune deficiency syndrome", American Journal of Ophthalmol, 101(4): 419-24 (1986).

Wax, "Is there a role for the immune system in glaucomatous optic neuropathy?", Curr Opin Ophthalmol, 11(2): 145-50 (2000).

Zambarakji et al., "Bilateral angle closure glaucoma in HIV infection", J R Soc Med, 89 (10): 581-2 (1996).

Zegans et al., "Transient vitreous inflammatory reactions associated witih combination antiretroviral therapy in patients with AIDS and cytomegalovirus retinitis", Am J Ophthalmol, 125(3): 292-300 (1998).

Pimentel et al., "Secondary Acute Angle Closure Glaucoma: A Complication of AIDS", Jour. of Emergency Medicine, vol. 15, No. 6, pp. 811-814 (1997).

Fellman et al., "Effects of Methotrexate Treatment on Serum Immunoreactivity of a Patient with Normal-Pressure Glaucoma", Amer. Journ. of Ophthalmology, vol. 127, No. 6, pp. 724-725 (1999).

Yang et al., "T Cell Subsets and sIL-2R/IL-2 Levels in Patients with Glaucoma", Amer. Journ. of Ophthalmology, vol. 131, No. 4, pp. 421-426 (2001).

* cited by examiner

VACCINATION AND IMMUNOTHERAPY AS NEW THERAPEUTIC MODALITIES IN THE TREATMENT OF GLAUCOMA

CROSS REFERENCE TO RELATED APPLICATIONS

This application claims priority to U.S. provisional application Ser. No. 60/492,151 filed Aug. 4, 2003, which is herein incorporated by reference.

BACKGROUND OF THE INVENTION

1. Field of the Invention

The present invention relates to a method of reducing intraocular pressure in mammalian subjects, particularly humans for treating and/or diagnosing glaucoma.

2. Background of the Related Art

In the United States, glaucoma is the second leading cause of legal blindness overall and the first leading cause of blindness in African-Americans. Primary open-angle glaucoma (POAG) is the most common form of glaucoma, and is widely recognized to affect 1-2% of the US adult population.

Glaucoma as an ophthalmologic disorder is responsible for significant visual impairment. The disease is characterized by progressive neuropathy caused in part by the deleterious effects of an increased intraocular pressure (IOP) on the optic nerve. In normal individuals, IOP ranges from 10 to 21 mm Hg. In contrast, in most individuals suffering from glaucoma, IOP is generally above 22 mm Hg. Loss of vision can also result from IOP only slightly above or even within normal range in patients with "normal-tension glaucoma."

Several different types of glaucoma exist, each having different a pathophysiology. Glaucoma may be either "primary" or "secondary." Primary glaucoma results from anatomical and/or physiological disturbances in aqueous fluid dynamics. This category includes primary open glaucoma (POAG), which constitutes the large majority of all glaucoma in the US. Angle-closure glaucoma results from blockage of the anterior chamber angle by another ocular structure (usually the iris), restricting the outflow of aqueous, and comprises a minority of glaucoma cases, but requires immediate attention. Secondary glaucoma occurs as a result of ocular injury or preexisting disease. Congenital glaucoma or infantile glaucoma is sometimes considered a third category. All types of glaucoma are thought to produce visual loss through the final pathway of optic neuropathy.

Glaucoma is associated with both non-pharmacological and pharmacological factors. Non-pharmacological factors include age, race, family history, diabetes, and hypertension. Pharmacological factors include the use of corticosteroids, which are thought to induce glaucoma by increasing resistance to outflow through the trabecular meshwork (TM).

Current glaucoma therapies are focused on either reducing intraocular pressure, or otherwise producing a "neuro-protective" effect, primarily on retinal ganglion cells. The main categories of therapy are surgical and pharmacological.

Both laser and regular (incisional) surgical procedures are used. Laser trabeculoplasty (LTP or SLT) or filtering surgery is used to improve aqueous drainage to reduce IOP. Problems with current surgical therapy include bleeding, infection, hypotony, loss of vision, decreasing effect over time, inability to titrate effect, and unpredictability.

Medications are also used to treat glaucoma. These may be topical or systemic agents. Glaucoma agents generally work by decreasing aqueous production, increasing aqueous outflow (via the trabecular and/or uveoscleral pathways), or a combination of both.

Problems with glaucoma medications include hyperemia, pain, headache, blurred vision, cataracts, retinal detachment, blindness, decreasing effect, dry mouth and nose, palpitation, tachycardia, hypertension, asthma, and other serious systemic side effects, including death. None of the currently used drugs is fully satisfactory. Besides the local and systemic toxicity mentioned above, many drugs have serious deleterious interactions with other drugs, and most drugs exhibit tachyphylaxis, or a decreasing effect with time. Moreover, current pharmacologic therapy also is often unable to lower IOP sufficiently to a level that prevents further visual loss due to glaucoma.

Many patients are already on "maximally tolerated medical therapy" without arresting their progressive visual loss due to glaucoma. Other patients are not candidates for surgery, for various medical or sociological reasons. Clearly, new treatment modalities and agents are needed for glaucoma patients, especially for those for whom current therapies are unable to stop progression of their disease towards eventual blindness.

There are few published reports regarding a possible immunologic basis for glaucoma. The great majority of the current literature reports negative evidence for an immunologic basis for glaucoma.

For example, patients with "chronic simple glaucoma," "low tension glaucoma," and "ocular hypertension" have been shown not to have a significantly different level of immunoglobulins compared to normal adult controls. In addition, no relationship has been shown between immunoglobulin levels and the severity of glaucoma as measured by visual fields and optic disc changes. Antinuclear antibodies have similarly not been found to correlate with the severity of glaucoma. The vast majority of glaucoma patients do not have an associated immune-related disease.

Recently, with the introduction of the new therapeutic class of prostaglandins and prostamides in the treatment of glaucoma (e.g., latanoprost (Xalatan, (TM)), bimatoprost (Lumigan (TM)), ophthalmologists have become more cognizant of the complicated role that inflammatory agents and anti-inflammatory agents play in the pathology, pharmacopathology, and pathophysiology of glaucoma. However, this recognition of the importance of inflammatory pathway modulation in the treatment of glaucoma has not lead to a similar recognition that immunologic modulation may be used to treat glaucoma, which is the underlying rationale for the present invention.

Because current teaching is that there is not a strong immunologic basis or etiology in the vast majority of glaucomas, the investigation for immunologic therapy for glaucoma has been largely ignored. Schwartz and colleagues have conducted studies on optic nerve crush injuries indicating that there may be an immunologic mechanism in the final pathway of ganglion cell damage in glaucoma that may be amenable to "rescue" or "neuroprotection" via immune therapy. They have also suggested that immune therapy may be used to moderate or mediate ganglion cell damage due to crush injury or other types of trauma, which they suggest may be helpful in treating optic neuropathies. However, they view this mechanism as totally separate from "hypotensive therapy" and do not consider the possibility that a vaccine may be used to create an immunologic response to lower IOP to treat glaucoma.

Even if most glaucomas do not have a primarily immunologic etiology, it may be possible that many types of glaucoma and glaucomatous neuropathy may be partially mediated by immunologic factors. For example, an immune mechanism may contribute to glaucomatous optic nerve damage. The immunologic response in glaucoma may be mediated by auto antibodies, or by a sensitizing antigen triggering an immune response that damages retinal ganglion cells. Such immunologic factors may be involved in many types of glaucoma, especially in "normal-tension" glaucoma. The immune system may also be involved in glaucoma by modulating cellular apoptosis and by other mechanisms of immune surveillance.

There are several reports in the literature associating HIV and/or AIDS with glaucoma. However, most of these are case reports of glaucoma caused by HIV and/or AIDS. For example, bilateral choroidal effusions with angle-closure glaucoma has been associated with HIV. In addition, bilateral angle-closure glaucoma has been associated with both HIV and AIDS, and when present in conjunction with uveal effusion has been reported as a presenting sign of HIV infection. Secondary acute angle closure glaucoma has also been reported as a complication of AIDS. High IOP, or secondary glaucoma, in response to HIV infection or AIDS is due largely to a mechanical mechanism (i.e., angle closure) and is noted here only to highlight the "teaching away" that prevented earlier recognition of the possible use immunotherapy as a treatment for glaucoma (rather than a cause of glaucoma).

Several investigators have noted sub-normal IOP (i.e., below 10 mm Hg) in AIDS patients. At first, it was thought that this was due to ophthalmic opportunistic infections in AIDS patients, such as cytomegalovirus (CMV) or *pneumocystis pneumoniae* (PCP) retinitis causing inflammation that impaired trabecular outflow, resulting in increased IOP. Later, clinicians reported sub-normal IOP in HIV patients without AIDS or any eye infections. Such reports were never pursued, however, as such patients generally saw well and were asymptomatic in their relatively hypotonous state, and so did not require therapy.

The scientific basis for this invention, therefore, involves an important clinical association that has been dismissed until the present invention as irrelevant: namely, that: 1) the low IOP seen in some HIV patients without AIDS is a result of the HIV virus having an immunologic effect on aqueous production and/or outflow, causing a decrease in IOP, and 2) a similar IOP-lowering effect can be achieved in glaucoma patients by stimulating an analogous immunologic response without causing HIV, AIDS or other immunologic disease, and 3) this immune-mediated IOP-lowering effect may be useful in the diagnosis of glaucoma suspects and/or treatment of glaucoma patients.

It is instructive to postulate some candidate mechanisms for the immunologic treatment of glaucoma. These include, but are not limited to, cellular or humoral immune mechanisms, lymphocytes including but not limited to T cells directed against ganglion cells, peptides, intermediate glutamate regulators or effectors, other antigens and/or antibodies, protein-mediated immunoreactivity, and other immune factors, mediators, modulators, and mechanisms.

SUMMARY OF THE INVENTION

The present invention consists of using immunologic therapy in the treatment of glaucoma. Specifically, the invention includes the use of a vaccine, viral derivative, particle, protein, antigen, antibody, or other immune-reactive substance to induce an immunologic response in a glaucoma patient to treat glaucoma, by lowering their IOP and/or through a neuro-protective mechanism It is postulated that the HIV virus induces an immunologic response that causes IOP reduction in otherwise-healthy HIV-positive, AIDS-negative patients by either reducing aqueous production, increasing aqueous outflow, or a combination of both. The present invention consists of inducing a similar response using immune-reactive agents, without causing the HIV infection or AIDS itself, for use as a new glaucoma therapeutic modality.

The mechanism is most likely a complicated one involving immunologic pathways, and may be due to either decreased aqueous production, increased aqueous outflow (either by the trabecular or non-trabecular outflow pathways, including uveal-scleral outflow), or a combination of the two.

This new inventive immunologic modality for glaucoma may have important benefits, including any or all of the following: It may be used as a primary therapeutic modality. It may be used as adjunctive or supplementary therapy. It may offer short-term, long-term, or even permanent efficacy. It may be used for prophylaxis to prevent the development of glaucoma. It may be used to diagnose glaucoma in patients suspected of having or developing glaucoma, via provocative testing or other means.

DETAILED DESCRIPTION OF THE PREFERRED EMBODIMENTS

Currently, many approaches are being employed in the attempt to create an AIDS vaccine. The multiple approaches represent attempts to replicate the body's immunologic response to the HIV virus, without inoculation with HIV, thereby conferring (partial or total, passive or active) immunity to HIV without subjecting the patient to actual HIV infection.

It is beyond both the scope of this patent and practicality to exhaustively list all possible methods to create candidate vaccines against AIDS. Nevertheless, it is instructive to list some of the most common approaches to creating AIDS vaccines, since some or all of the HIV analogues so produced may be useful in the treatment of glaucoma:

1. Naked DNA: Harmless DNA from HIV is injected or otherwise delivered via a viral or other vector, and is taken up by cells, which make HIV proteins that stimulate the production of antibodies to block infection and/or killer cells to control infection, and/or induce an immunologic response that decreases IOP and is useful for glaucoma therapy.

2. Proteins: A harmless portion of HIV, e.g., a surface protein, is delivered to stimulate the production of antibodies that can block infection, and/or induce an immunologic response that decreases IOP and is useful for glaucoma therapy.

3. Live vectors: Genetically engineered viruses or bacteria or other organisms carry HIV genes into cells to stimulate killer cells, and/or induce an immunologic response that decreases IOP and is useful for glaucoma therapy.

4. Live/weakened/attenuated virus: A live but weakened or attenuated form of HIV is used to induce immunity in the host, and/or induce an immunologic response that decreases IOP and is useful for glaucoma therapy.

5. Killed virus: A killed virus or other organism, either by heat, radiation, chemicals, or other methods, is used to induce immunity in the host, and/or induce an immunologic response that decreases IOP and is useful for glaucoma therapy.

6. Combination therapy: Any and all of the above methods may be used in combination to induce the desired immune response. For example, a combination of proteins or naked DNA can be used in combination with live vectors to stimulate the immune system, and/or induce an immunologic response that decreases IOP and is useful for glaucoma therapy.

Note that an important aspect of the current invention is that it may allow for the use of HIV and AIDS vaccines or other immunologic modalities in the treatment of glaucoma, even in those cases where such vaccines or immunologic modalities have been shown to fail as efficacious in AIDS vaccination, or the original intended use.

By 2000, over 60 phase I/II human trials of 30 candidate HIV vaccines have been conducted worldwide. Again, it is beyond the scope of this patent to cover each exhaustively. The present invention anticipates using any of these and/or future such vaccines (even one that has failed trials for efficacy against preventing HIV infection) for the treatment or prevention of glaucoma or ocular hypertension (perhaps in a modified form, method of administration, or dosage) by the mechanism of lowering IOP or offering neuroprotection.

Importantly, over $1 billion US has been spent already by private companies in the pursuit of a successful AIDS vaccine, none of which has yet been shown to have sufficient efficacy for approval. If any one of these "failed vaccines" can be shown by the present invention to be beneficial as a glaucoma treatment, it would be of great benefit to mankind. Moreover, by recouping its research and development costs, the vaccine company would be able to continue to fund the critical search for the world's first successful vaccine against AIDS.

In addition, the present invention anticipates the use of measuring IOP in HIV-positive and AIDS patients as an inexpensive and noninvasive measure of their immunologic status and response to AIDS vaccines and other treatment modalities, instead of invasive blood testing.

The dosage of vaccination, including, for example, the dose of "priming" with (probable recombinant) viral vector and "boosting" doses of (probable recombinant) viral protein, will most likely be similar in the application of glaucoma treatment and/or prevention as that for protection against HIV, but may be appropriately modified (either increased, decreased, or given on an altered regimen) to maximize the pressure-lowering and/or neuroprotective effects and minimize the incidence and severity of ocular and systemic side effects.

A partial list of HIV vaccines that either have or may in the near future undergone human trials, any of which or a modification or combination of which may be used as part of the present invention, is given in the following table:

TABLE 1

AIDS vaccines potentially suitable for use as a novel glaucoma therapy

| Manufacturer/Sponsor | Candidate HIV/AIDS vaccine |
| --- | --- |
| AlphaVax | VEE replicon-gag only (clade C) and gag, env, pol (clade C) |
| ANRS (France) | lipopeptides LP5, LP6 |
| Antigenics | QS-21 (adjuvant) |
| Apollon | DNA (B) |
| Aventis Pasteur | vCP205, 1433, 1452, 1521(E), and 1452-A, lipopeptides, gp160, gp160-did (E), pseudoviron therapore-p24 |
| Avant | |
| Bioption | SFV replicons containing HIV genes |
| British Biotech | p17, p24, Ty-VLP, p24-VLP |
| Cell-Sci | HGP30W peptide |
| Chemo-Sero-Ther.Res.Inst. | proteins derived from V3 domain |
| Chiron | gp120 (B), gp120 (B)(E), p24, DNA, alphavirus replicons, oligomeric envelope, including adjuvants |

TABLE 1-continued

AIDS vaccines potentially suitable for use as a novel glaucoma therapy

| Manufacturer/Sponsor | Candidate HIV/AIDS vaccine |
| --- | --- |
| Emory University | gag-pol-Enc DNA/MVA |
| Epimmune | DNA-multi-epitope |
| GeneCure | replication-defective HIV |
| GlaxoSmithKlein | recombinant proteins in novel MPL-like adjuvants |
| GlobeImmune | HIVAX-2; gag/cytosolic protein |
| Hesed Biomed | covalently reactive antigen analog (CRAA) |
| HIV-VAC/Birmingham | NFU.Ac.HIV (intracellular) |
| ID Vaccine/Yeshiva U. | gp120 peptides, multivalent with PPD adjuvant |
| Immune Research Corp. | whole-killed stripped of envelope |
| Immunotech | anti-idiotype monoclonal antibody against CD4 |
| Institute of Human Virology | DNA/MVA; orally administered, Salmonella-weakened |
| MaxPharma/CEL-SCI | HGP-30 |
| Merck | DNA, viral vector |
| PowderJet; IDT/Oxford U. | DNA + MVA (polyepitope + gag, clade A) |
| Progenics | envelope-based |
| Protein Sciences | p55 particle |
| St. Jude Hospital | multi-envelope (gp120 and gp41 variants) |
| Targeted Genetics | adeno-associated virus-gag (A, C) |
| Therion | TCB-IIIB; vaccinia-env, gag, pol, fowlpox-multigene MVA-multi-gene, MVA-gag/pol |
| United Biomedical | synthetic antigen from MN strain of HIV |
| VaxGen/(Genentech) | AIDSVAX gp120 (B/B) and gp120 (B/E), gp120 (A, C, D) |
| Viscal | DNA-multigenic, particle forming |
| Virax | DNA + fowlpox – multigenic + IL-12 or Ifg |
| WRAIR/NIH | MVA-CMDR |
| Wyeth-Lederle | APL-400-047 and -003, gp120 C4-V3 with adjuvants |

The above list represents the most clinically and commercially promising AIDS vaccines. Many additional candidate HIV vaccines in earlier stages of development exist, any of which or a modification or combination of which may be used as part of the present invention. Again, it is beyond the scope of this patent to list every possible candidate vaccine that may be suitable for application according to this invention; a more complete listing can be found in the Jordan Report Accelerated Development of Vaccines available from the National Institute of Health, which report, as well as all other references cited in this application, are incorporated by reference herein as if fully set forth. However, a partial list useful for illustrative purposes for those skilled in the art is given in the following table:

TABLE 2

AIDS vaccine candidates potentially suitable for use as a novel glaucoma therapy Subunits:
Vaccine Candidate:

Rgp 160, rgp 160 (VaxSyn ™), rgp 160 oligomeric, rgp 120 Bivalent Clade B (AIDSVAX ™), rgp 120 Bivalent Chade B/E, rgp 120 (Env 2-3), rp 24, rRT, RT-VCG, tat/chemically inactivated (toxoid)
Expression System/Production Method:

Vaccinia/mammalian cell, baculovirus/insect cell, Chinese hamster ovary cell, yeast, recombination, E. coli plasmid/Vibrio cholera, carboxymethlyated tat
HIV Strains:

MN/BRU, MN/LAI, LAI (group of closely related HIV isolates that includes LAV, IIB, BH10 and BRU), IIIB (LAI), MN, LAV (IIIB), Thai Clade E, GNE8, A244, GM-CSF, SF-2, CM235, W61D, US4

TABLE 2-continued

AIDS vaccine candidates potentially suitable
for use as a novel glaucoma therapy Adjuvant or Delivery System:

Alum, IFA, polyphosphazene, alum, DOC, IFA, ISA724, oil/water,
3-deacyl monophosphoryl lipid A, MPL, MPL-AF, RIBI,
polyphosphazene, proteosomes, liposomes, emulsomes, *cholera* toxin B,
QS-21, MF59 +/− MTP-PE, SAF-2 +/− MDP, QS21 + MPL, *V. cholera*
ghosts (VCG), ISA 51
Peptides:
Vaccine Candidate:

V3-T helper epitope peptides (PCLUS 3-18 MN, PCLUS 6-18 MN),
V3 sequences in single peptide (TAB9), C4-V3 peptides
(T1SP10 MN(A)), p17-KLH (HGP-30W ™), p24-V3 peptide,
V3-MAPS, octameric, monovalent (Synvac ™), V3-MAPS, octameric,
multivalent, V3-MAPS, microparticulate, monovalent, V3 linear peptide,
V3 peptide (RP400c), V3-PPD, multivalent V3 peptide coupled to PPD,
V3 peptide coupled to *Mycobacterium* protein, V3 PND, Th epitopes, gag-
lipopeptide (P34541b), lipopeptides + nef (2), gag (2) and V3 peptides,
gag, pol and nef (2), peptides + tetanus toxoid, peptide (LIPO-6T), pol-
tetanus toxoid, polypeptide (CY2301), gp120, gp41, gag p7 peptides,
V3-HA, V3 loop-T helper epitope peptides, conformationally constrained,
V3-CD4 binding site-gag peptides, Multicomponent (VC1), p24,
HGP-30W ™, HIV-Peplotion ™
Expression System/Production Method:

Synthetic chimeric, Recombinant *E. coli*, Synthetic p17 peptide coupled
to Keyhole Limpet Hemocyanin (KLH) carrier protein, V3 peptide
coupled to *Pseudomonas aeruginosa* toxin A, Recombinant baculovirus,
HIV-1/mammalian cell treated with detergent.
Adjuvant or Delivery System:

IFA, Montanide-ISA720, alum, QS21, 10K *Mycobacterium*, lipopeptide,
CFA, GB8, MN
Particles:
Vaccine Candidate:

Remune ™, HIVIONS, p24 VLP, env, gag, pol pseudovirons, p55 gag
particle, HIV-1,
Expression System/Production Method:

Stabilized with formaldehyde, baculovirus/insect cell, vaccinia/
mammalian cell, V3-peptide + yeast, inactivated with betapropiolactone
and irradiation
HIV Strains:

HZ321, LAI, BX08, MN, RF, IIIB, LAI/MD, primary
Adjuvant or Delivery System:

IFA, P40, QS-21, alum, hepatitis B core antigen, Digitonin, CFA
Recombinant live vector:
Vaccine Candidate:

Adenovirus-HIV-1 env, ALVAC-HIV gp 160 (vCP 125), ALVAC-
HIV env, gag, protease (vCP 205), ALVAC-HIV env, gag, protease
and pol and nef epitopes (vCP 300), ALVAC-HIV env, gag, protease
and pol and nef epitopes (vCP 1433), ALVAC-HIV env, gag, protease
and pol and nef epitopes (vCP 1452), vCP 1551, BCG-HIV-1 env
peptides, BCG-V3, rBCG-THA13, poliovirus-HIV-1, VVH203, SFV-
HIV-1, TBC-3B, HIVAC-1e ™, NYVAC, *Salmonella*-HIV-1 V3
peptide
Expression System/Production Method:

Recombinant adenovirus, attenuated recombinant canarypox,
recombinant BCG, recombinant *B. abortus*, recombinant Fowlpox,
HRV14, CVD 908 vaccine strain, recombinant SFV, recombinant
vaccinia, recombinant vesicular stromatitis virus
HIV Strains:

MN, MN/LAI, Clade E/B, Clade A, LAI, LAV-1 (LAI), LAV
(IIIB), 89.6
Adjuvant or Delivery System:

GM-CSF, none

Again, it is beyond the scope of the present invention to be either exhaustive or complete regarding all iterations of possible vaccine candidates that may be successful for use in treating glaucoma. For example, iterations similar to those given in Table 2 above may be given for vaccine candidates comprised of DNA and/or cellular components. Thus, Table 2 should be understood to be merely a representative sampling of those vaccine candidates that can be used with the present invention. Therefore, the scope of the present invention is not to be limited by the aforementioned examples. It may be desired to provide an inventive composition that combines some, but not all, of the aforementioned components.

II. Other Candidate Immunotherapeutic Agents:

It is assumed that the most preferred composition will involve a HIV or AIDS vaccine or component thereof, to lower IOP for the treatment of glaucoma. However, besides vaccines, the present invention anticipates the use of proteins, polynucleotides, prions, nucleotides, amino acids, and other agents as candidate immunotherapeutic agents with biological activity that causes an immune reaction that lowers IOP or has a neuro-protective effect beneficial in the treatment of glaucoma.

Moreover, besides the use of vaccines designed for AIDS prevention to induce an immune response which lowers IOP for the treatment of glaucoma, the present invention anticipates the use of therapeutic AIDS vaccines for the same novel therapeutic use in glaucoma. A continuously updated list of both candidate prophylactic and therapeutic AIDS vaccines is given in the website of the National Institutes for Health (NIH) relating to AIDS information or AIDSinfo, as well as the website of the Pharmaceutical Research and Manufacturers of America (PhRMA).

III. Method of Identifying Candidate Vaccine for use in Glaucoma Treatment:

The current invention acknowledges that the de novo development of a new vaccine for the treatment of glaucoma will be very time-consuming and expensive. Therefore, the preferred embodiment of the inventive vaccine will be one that has already undergone or is undergoing US FDA trials as an AIDS/HIV vaccine. An outline for identifying such a candidate vaccine for use in lowering IOP as a glaucoma treatment is provided herein.

The preferred candidate vaccine will be selected from a list of all prophylactic and therapeutic AIDS/HIV vaccines currently in development and/or undergoing clinical trials. Lists of such vaccines and vaccine trials are given in the website of the NIH under its AIDS info section, in the website of the PhRMA, and the National Institute of Allergy and Infectious Diseases.

A test of intraocular pressure (IOP), most likely applanation tonometry, will be added to the battery of tests during one or more of the clinical trials for AIDS/HIV vaccines. IOP will be tested upon study enrollment, or at least before administration of the vaccine, to establish a baseline IOP. IOP will then be measured at various time points after administration of the vaccine and/or any booster doses, to check for pressure-lowering effect of the vaccine. Statistical tests will be used to determine statistical significance of IOP-lowering effect of study patients compared to control patients.

Other assays may be used to correlate IOP-lowering effect with immune function, such as blood tests for CD4 levels, viral load, antigen, antibody, complement, and other tests.

Once an AIDS/HIV vaccine has been identified that induces a pressure-lowering response, a separate clinical trial will be designed and conducted to meet US FDA requirements. If the candidate vaccine has already passed UD FDA Phase I and/or II for another indication, it may be possible to run only a new Phase III trial to determine vaccine efficacy at lowering IOP for the use as novel glaucoma therapy.

IV. Method of Administration:

The current invention includes administration of any prophylactic or therapeutic AIDS/HIV vaccine, other vaccine, or immunologic agent, including but not restricted to any HIV analogue, HIV part (including but not restricted to DNA, protein, or other pieces or particles), or weakened, killed, or otherwise inactivated form of HIV, or other immunologically active protein, peptide, prion, antigen, antibody, or agent for the purpose of causing an immune reaction which decreases intraocular pressure (IOP) or has a neuro-protective effect beneficial in the treatment of glaucoma.

The method of administration or delivery may be by, but is not limited to, direct inoculation, by viral or other type of vector, possibly in conjunction with gene transfer, or by any other reasonable means, either systemically or locally. If given systemically, which is most likely, the inventive agent may be given by injection, inhalation, sublingually, subcutaneously, submucosaly, orally, or my other accepted means of systemic administration. If given locally, which is less likely, the inventive agent may be administered in or around the eye as an injection, solution, ointment, cream, suspension, gel, or sustained release vehicle, or may be given locally via the intramuscular, subcutaneous, intramedullar, intrathecal, intraventricular, intraperitoneal, or other routes. The invention includes and anticipates the use of reasonable adjuvants, excipients, and other additives or preservatives necessary to obtain the desired response.

The invention includes the administration of any AIDS vaccine or HIV virus analogue or component, separately or in any combination, to decrease IOP. It should also be noted that the invention includes any permutations for combining some or all of the above components, as long as the desired effect is to reduce IOP.

While the invention has been shown and described herein with reference to particular embodiments, it is to be understood that various additions, substitutions, or modifications of form, arrangement, proportions, components, methods of administration, and otherwise, used in the practice of the invention and which are particularly adapted to specific environments and operative requirements, may be made to the described embodiment without departing from the spirit and scope of the present invention.

In particular, any pharmaceutical compositions for use in accordance with the present invention may be formulated in a manner using one or more physiologically acceptable carriers, excipients, or auxiliaries that facilitate processing of the active compounds into preparations that can be used pharmaceutically. The pharmaceutical composition of the present invention may also contain stabilizers, preservatives, buffers, antioxidants, or other additives known to those skilled in the art.

The pharmaceutical composition of the invention may be in the form of a complex of the proteins or protein or peptide antigens, with suitable lipids or liposomal formulations is The invention is also valuable for veterinary applications including glaucoma in animals.

V. Effective Dosage:

The invention includes any pharmaceutical compositions suitable for use wherein the active ingredients are contained in an effective amount to induce an immunologic response in a glaucoma patient to decrease IOP or otherwise achieve a neuro-protective effect beneficial in treating glaucoma. In addition, the invention includes any effective dosage that may be used in a glaucoma suspect as a provocative or other test to cause an immune response and effect helpful in diagnosing glaucoma or identifying those at risk for developing glaucoma.

VI. Method of Usage:

The invention would be used to treat glaucoma or ocular hypertension in a manner similar to other accepted modalities of glaucoma treatment, particularly medications or laser. For the possible use as a preventative vaccine for glaucoma, the method of usage of the invention is somewhat different, but retains certain similarities as the method of usage and administration for use as a therapeutic agent in glaucoma, as described below.

First, a diagnosis of glaucoma or ocular hypertension or glaucoma suspect would be made by the doctor via accepted methods, including any or all of the following tests: baseline determination of slit lamp exam, gonioscopy, IOP, visual fields, cup-to-disk ratio (CDR), central corneal thickness (CCT), and other tests such as GDX or HRT. Based on these tests and other factors such as race and family history, the doctor will make a determination if the patient is a glaucoma suspect, ocular hypertensive, or has glaucoma.

If the patient is a glaucoma suspect, the doctor may elect to follow the patient with "watchful waiting" rather than treatment, and observe for progression of abnormalities on any of the above tests. Alternatively, the doctor may elect to administer the inventive glaucoma vaccine to either reduce IOP immediately, or otherwise subsequently reduce the risk of developing the characteristic visual field defects, cupping, loss of nerve fiber layer, or other abnormalities associated with glaucoma.

If the patient is classified as an ocular hypertensive or glaucoma patient, the doctor may elect to administer the inventive glaucoma vaccine either as primary or secondary therapy, either alone or in combination with other modalities such as glaucoma medications or laser treatment (e.g., ALT or SLT laser) or glaucoma surgery.

The usage of the glaucoma vaccine in these cases would be as follows. After establishing the patient's baseline function on all tests, the invention would be administered via the approved route. IOP, visual fields, GDX, HRT, and other relevant tests would then be used to follow these patients for response to glaucoma vaccine therapy. In addition, certain other tests of immune function would be assessed to ascertain if the desired immune response was achieved by the glaucoma vaccine; possible measures include measurements of specific antigens, antibodies, immunoglobulins, blood cell counts, complement, proteins, and other blood tests and tests of immune response and function.

Using this information, the doctor will assess whether the patient has had a positive response to glaucoma vaccine therapy, and when additional doses or treatments will be necessary. Such additional doses may be given when tests show progression of glaucomatous damage, increase in IOP, decreases in desired immune response, or merely based on a schedule according to previously-determined average patient responses to therapy. In addition, adjunctive therapy with medicines and/or laser surgery and/or surgery would be considered by the doctor to optimize the control of glaucoma.

Glaucoma vaccine administration would be contraindicated in persons who had a known adverse reaction or allergy to any of the components in the vaccine, or to similar vaccines. Further therapy with the glaucoma vaccine would be curtailed if any serious side-effects occurred or if the effect of the vaccine wore off and could not be reestablished with further doses or increasing doses of the glaucoma vaccine product.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

I claim:

1. A method for therapeutic treatment of glaucoma or ocular hypertension comprising administering to a human subject a composition containing an effective amount of an isolated HIV gp120 protein to decrease intraocular pressure, wherein said subject has an intraocular pressure (IOP) of 22 mm Hg or greater.

2. The method of claim 1, further comprising performing a diagnostic test on the subject to determine the effect of said composition on reduction of IOP in said human subject.

3. The method of claim 2, wherein the diagnostic test comprises one or more tests selected from the group consisting of slit lamp examination, gonioscopy, measuring intraocular pressure, visual field examination, cup-to-disk ratio determination, central corneal thickness determination, scanning laser polarimetry (SLP) and heidelberg retina tomograph (HRT).

4. The method of claim 1, wherein the step of administering comprises systemic or local inoculation.

5. The method of claim 4, wherein systemic inoculation is performed by one or more of injection, inhalation, sublingual administration, subcutaneous administration, submucosal administration, or oral ingestion.

6. The method of claim 4, wherein the local inoculation is performed in, or in the vicinity of, the eye.

7. The method of claim 4, wherein the local inoculation is performed via intramuscular, intramedullary, intrathecal, intraventricular, or intraperitoneal routes.

8. The method of claim 1, wherein said effective amount of said gp 120 is sufficient to reduce intraocular pressure to below 22 mm Hg.

9. The method of claim 1, wherein the composition further includes additives selected from a group consisting of adjuvants, excipients, preservatives and combinations thereof.

10. A method for reducing intraocular pressure in a human subject, comprising a) determining whether the subject has an intraocular pressure of 22 mm Hg or greater; and b) administering a composition containing an isolated HIV gp120 protein to a human subject that has an intraocular pressure of 22 mm Hg or greater.

11. The method of claim 10, wherein said human subject that has an intraocular pressure of 22 mm Hg or greater prior to administering said composition has lower intraocular pressure than 22 mm Hg after said administration.

* * * * *